United States Patent [19]

Hutton

[11] 4,317,781

[45] Mar. 2, 1982

[54] PROCESS FOR THE MANUFACTURE OF P-HYDROXYBENZYL CYANIDE

[75] Inventor: Jonathan Hutton, Adlington, England

[73] Assignee: Imperial Chemical Industries Limited, London, England

[21] Appl. No.: 253,267

[22] Filed: Apr. 13, 1981

[30] Foreign Application Priority Data

Apr. 23, 1980 [GB] United Kingdom ............... 13325/80

[51] Int. Cl.$^3$ ................... C07C 120/06; C07C 121/75
[52] U.S. Cl. ................................................. 260/465 F
[58] Field of Search ..................................... 260/465 F

[56] References Cited

U.S. PATENT DOCUMENTS 3,983,160 9/1976 Merger ............................ 260/465 F
4,154,758 5/1979 McMenim ...................... 260/465 F

FOREIGN PATENT DOCUMENTS 1476073 6/1977 United Kingdom .

OTHER PUBLICATIONS

Schwartz, et al., J. Org. Chem., vol. 41, No. 14, pp. 2502-2503 (1976).

*Primary Examiner*—Dolph H. Torrence
*Attorney, Agent, or Firm*—Cushman, Darby & Cushman

[57] ABSTRACT

An improved process for the preparation of p-hydroxybenzyl cyanide by the reaction of p-hydroxybenzyl alcohol with an alkali metal cyanide, by carrying out the process in the presence of an alkyl formate, especially n-propyl formate. The cyanide product is a valuable intermediate for the preparation of the $\beta$-adrenergic blocking agent atenolol.

10 Claims, No Drawings

PROCESS FOR THE MANUFACTURE OF p-HYDROXYBENZYL CYANIDE

This application relates to a chemical process for the manufacture of p-hydroxybenzyl cyanide.

It is known from United Kingdom Specification No. 1,476,073, that p-hydroxybenzyl cyanide may be obtained by the reaction of p-hydroxybenzyl alcohol with hydrogen cyanide. The described process is carried out under acidic conditions whereby the hydrogen cyanide is released from an alkali metal cyanide in situ. The yield quoted for the reaction, in Example 3 of said specification, is 54%.

It is further known, from the Journal of Organic Chemistry, 1976, 41, 2502-2503, that p-hydroxybenzyl cyanide may be obtained by the reaction of p-hydroxybenzyl alcohol with sodium cyanide in solution in N,N-dimethylformamide, at a temperature of 110°-130° C. The yield quoted for this reaction is 67%.

We have now found, and herein lies our invention, that the conversion of p-hydroxybenzyl alcohol to p-hydroxybenzyl cyanide is much improved if the alcohol is reacted with an alkali metal cyanide in the presence of an alkyl formate.

According to the invention there is provided a process for the manufacture of p-hydroxybenzyl cyanide having the formula:

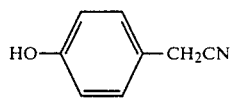

which comprises the reaction of p-hydroxybenzyl alcohol having the formula:

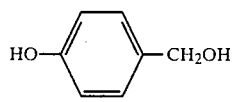

or a lower carboxylic ester or a borate ester thereof, with an alkali metal cyanide in the presence of an alkyl formate having the formula

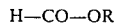

H—CO—OR wherein R is alkyl of up to 6 carbon atoms.

A suitable alkali metal cyanide is, for example sodium or potassium cyanide. The former of these is preferred.

A suitable alkyl formate is, for example, methyl, ethyl or n-propyl formate. The last-mentioned of these is preferred.

A suitable lower carboxylic ester of the p-hydroxybenzyl alcohol is, for example, a formate or acetate ester.

The reaction may be carried out in a high-boiling dipolar aprotic solvent, for example N,N-dimethylformamide, N,N-dimethylacetamide, dimethylsulphoxide or N-methyl-2-pyrrolidone. Alternative solvents such as cellosolve or 1,2-dimethoxyethane may also be used.

The reaction is preferably carried out at a temperature of between 20° and 135° C., especially between 65° and 70°.

The p-hydroxybenzyl alcohol is preferably prepared in situ by the reduction of p-hydroxybenzaldehyde, especially if this reduction is carried out by means of an alkali metal borohydride, for example sodium borohydride, as this reduction provides initially the borate ester of the p-hydroxybenzyl alcohol.

p-Hydroxybenzyl cyanide is a valuable intermediate for the manufacture, by hydrolysis, of p-hydroxyphenylacetamide, itself a valuable intermediate for the preparation of the β-adrenergic blocking agent atenolol.

The invention is illustrated but not limited by the following Examples:

EXAMPLE 1 n-Propyl formate (264 g.) and granular sodium cyanide (150 g.) were added successively to a stirred suspension of p-hydroxybenzyl alcohol (310 g.) in N,N-dimethylformamide (148 g.) and the mixture was heated at 67°-68° C. for 1 hour, cooled to 40° C. and poured into water (588 ml.). The mixture was cooled to 20°-25° C., the pH of the mixture was adjusted from 9.5 to 4.0 with 98% formic acid (270 ml.), and the mixture was extracted three times with isobutyl methyl ketone (677 ml, 196 ml. and 196 ml. successively). Each extract was washed twice with water (196 ml. each time) and the combined extracts were dried by azeotropic distillation under reduced pressure at 60°-70° C. There was thus obtained p-hydroxybenzyl cyanide (319 g., 96% yield).

EXAMPLE 2

A solution of sodium borohydride (3.92 g.) in dimethylformamide (30 ml.) was added during 25 minutes to a powerfully-stirred solution of p-hydroxybenzaldehyde (30.5 g.) in dimethylformamide (30 ml.) which was maintained at 60° C. under an inert atmosphere, and the mixture was stirred for a further 60 minutes during which time it became very viscous. n-Propyl formate (29.4 ml.) and sodium cyanide (15 g.) were added and the mixture was stirred for 2 hours at 60° C. and then kept for 17 hours at laboratory temperature. Water (59 ml.) and isobutyl methyl ketone (67.5 ml.) were added, the mixture was adjusted to pH 6 with formic acid and then stirred for 1 hour, and the phases were separated. The aqueous phase was extracted twice with isobutyl methyl ketone (20 ml. each time) and the organic phase was washed with water (30 ml.). The three organic solutions were combined, washed with water and evaporated to dryness under reduced pressure at 60° C. The residual oil was shown by gas-liquid chromatography to contain a 91% yield (based on the p-hydroxybenzaldehyde used) of p-hydroxybenzyl cyanide and was hydrolysed to p-hydroxyphenylacetamide without further purification.

What we claim is:

1. A process for the manufacture of p-hydroxybenzyl cyanide having the formula:

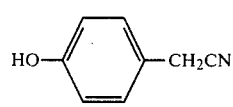

which comprises the reaction of p-hydroxybenzyl alcohol having the formula:

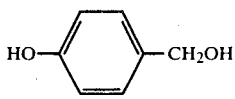

or a lower carboxylic ester or a borate ester thereof with an alkali metal cyanide in the presence of an alkyl formate having the formula:

H—CO—OR wherein R is alkyl of up to 6 carbon atoms.

2. A process as claimed in claim 1 wherein the alkali metal cyanide is sodium or potassium cyanide and wherein the alkyl formate is methyl, ethyl or n-propyl formate.

3. A process as claimed in claim 2 wherein the alkali metal cyanide is sodium cyanide.

4. A process as claimed in claim 2 or 3 wherein the alkyl metal formate is n-propyl formate.

5. A process as claimed in any one of claims 1 to 4 wherein the lower carboxylic ester of the p-hydroxybenzyl alcohol is the formate or acetate ester.

6. A process as claimed in any one of claims 1 to 5 which is carried out in a high-boiling dipolar aprotic solvent.

7. A process as claimed in claim 6 wherein the solvent is N,N-dimethylformamide, N,N-dimethylacetamide, dimethylsulphoxide or N-methyl-2-pyrrolidone.

8. A process as claimed in any of claims 1 to 7 which is carried out at a temperature of between 20° and 135° C.

9. A process as claimed in claim 8 wherein the temperature is between 65° and 70° C.

10. A process as claimed in any of claims 1 to 4 or 6 to 9 wherein the p-hydroxybenzyl alcohol is prepared in situ by the reduction of p-hydroxybenzaldehyde by means of sodium borohydride.

* * * * *